United States Patent [19]

Biedermann et al.

[11] Patent Number: 5,041,113
[45] Date of Patent: Aug. 20, 1991

[54] STABILIZATION MEMBER FOR STABILIZING BONES

[76] Inventors: Lutz Biedermann, Am Schäfersteig 8, D-7730 VS-Villingen; Jürgen Harms, Belchenweg 9, D-7517 Waldbronn-Reichenbach, both of Fed. Rep. of Germany

[21] Appl. No.: 552,776

[22] Filed: Jul. 16, 1990

[30] Foreign Application Priority Data

Jul. 20, 1989 [DE] Fed. Rep. of Germany ....... 3923995

[51] Int. Cl.⁵ .................... A61B 17/56; A61B 17/58
[52] U.S. Cl. .................................... 606/61; 606/71
[58] Field of Search ................ 606/60, 61, 65, 66, 606/69–71; 623/16, 17; 128/69; 129/69

[56] References Cited

U.S. PATENT DOCUMENTS

| 3,547,114 | 12/1970 | Haboush | 606/71 |
| 4,388,921 | 6/1983 | Sutter et al. | 606/71 |
| 4,683,878 | 8/1987 | Carter | 606/69 |
| 4,913,134 | 4/1990 | Luque | 606/61 X |

FOREIGN PATENT DOCUMENTS

| 0263938A2 | 4/1988 | European Pat. Off. | |
| 0290138 | 11/1988 | European Pat. Off. | 606/69 |
| 3027148A1 | 12/1981 | Fed. Rep. of Germany. | |
| G8610858.1 | 7/1986 | Fed. Rep. of Germany. | |

*Primary Examiner*—Ronald Frinks
*Attorney, Agent, or Firm*—Donald Brown

[57] ABSTRACT

The invention refers to a stabilization member serving for fixing broken or partly cracked bones in a predetermined position during the healing process or an even longer period. The stabilization member comprises a bar having elongated holes and the bar is fastened to the bone part to be stabilized by means of screws extending through the elongated holes. It is a drawback of such conventional stabilizing members that generally the screws can not be screwed in a direction perpendicular to the bar, because the screwing direction depends on the direction and form of the bone part. It is therefore intended to modify this conventional design such that a strong connection is obtained even in case that the screw does not extend in a direction perpendicular to the bar. To this end an intermediate piece is provided for each screw and the intermediate piece has one side resting on the bar and the other side being provided with a spherical segment-shaped recess receiving the spherical segment-shaped lower portion of the screw head.

10 Claims, 3 Drawing Sheets

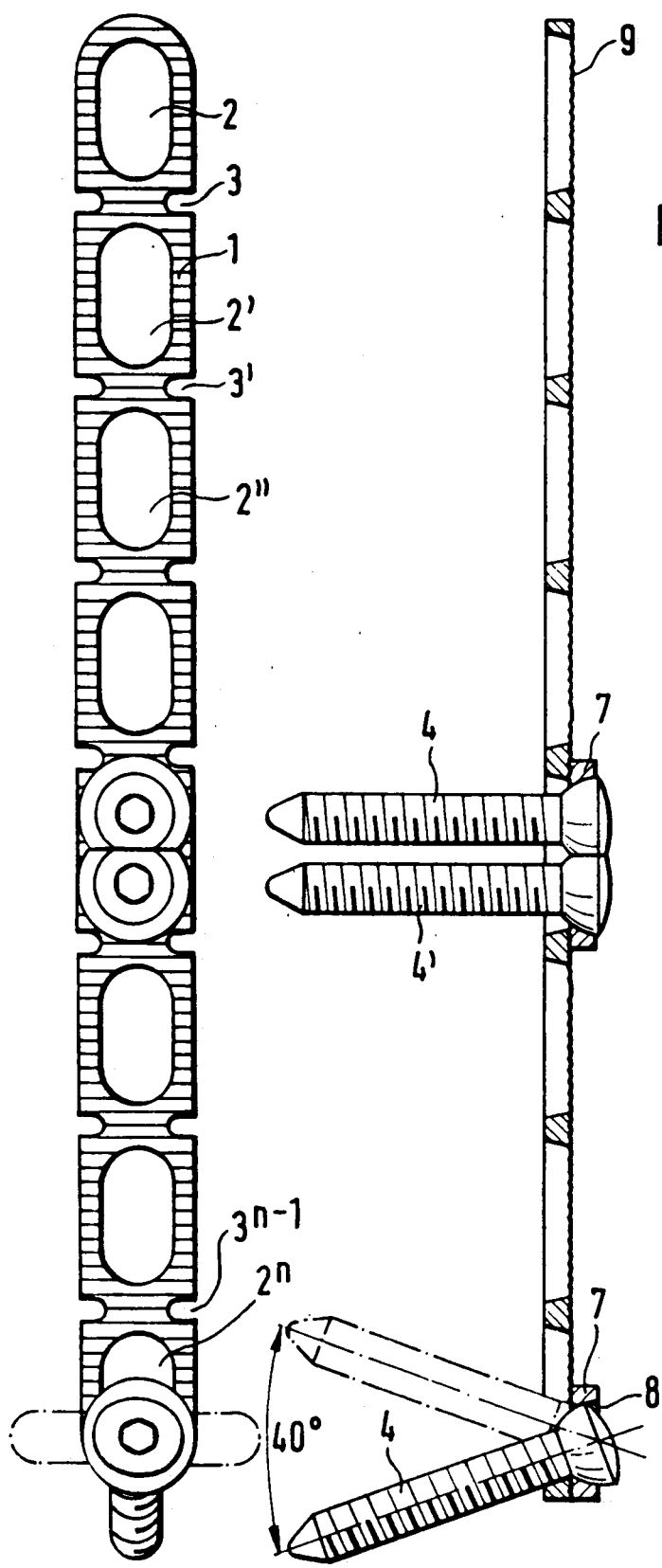

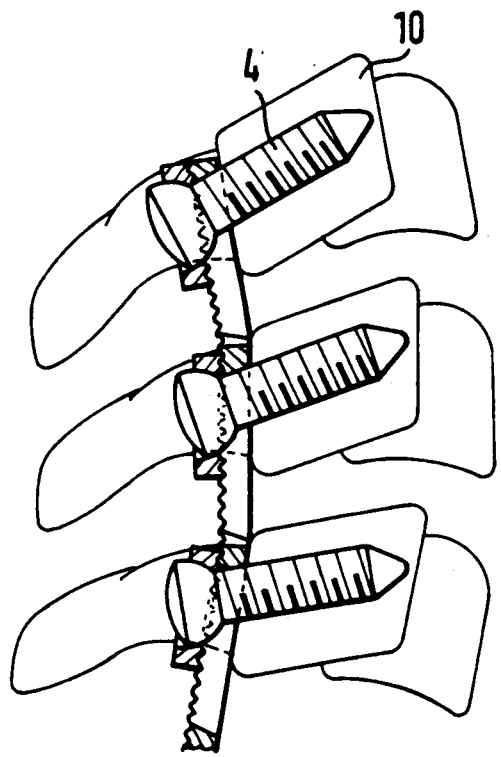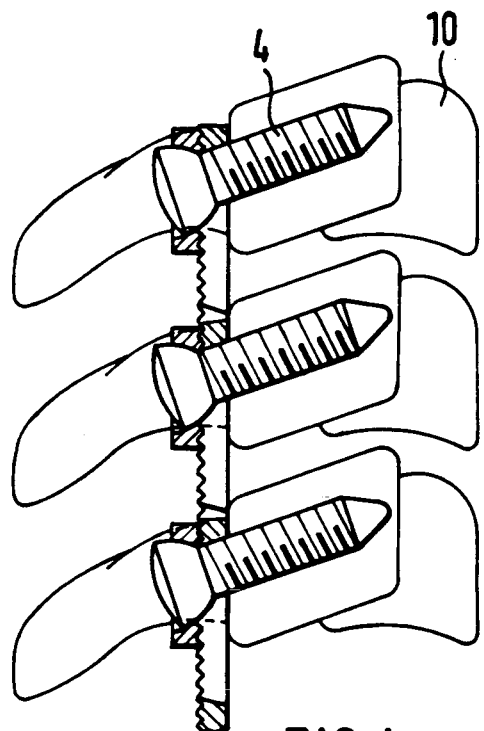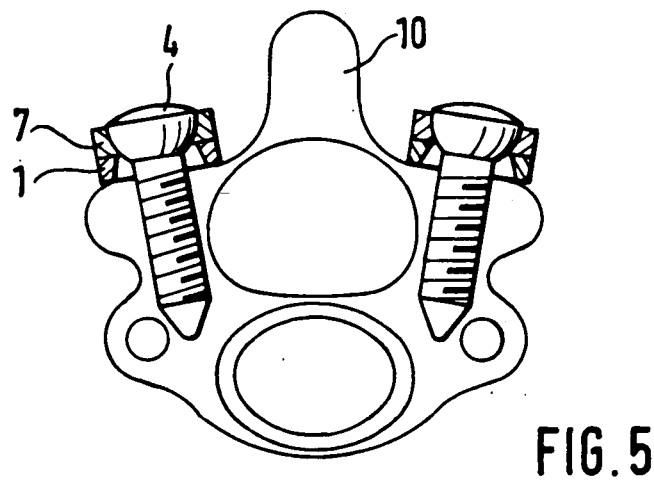

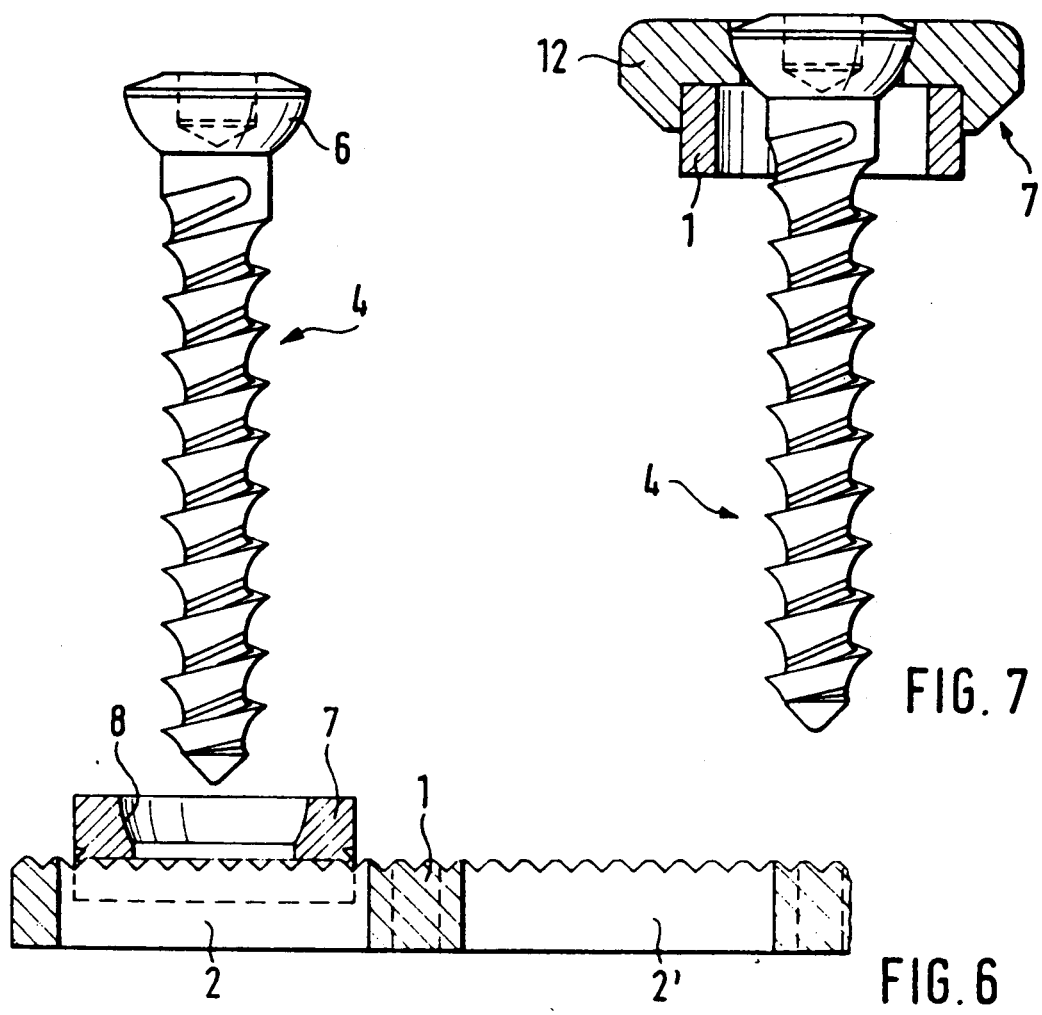
FIG. 7
FIG. 6
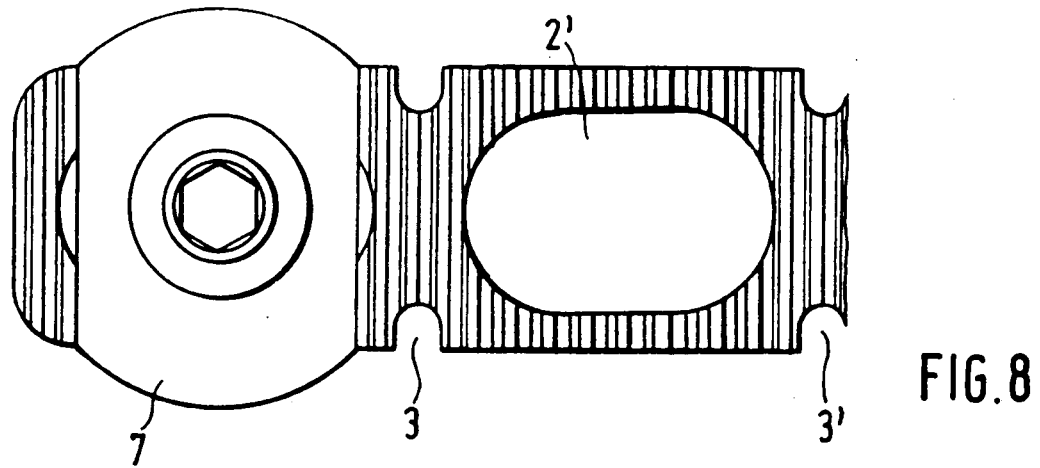
FIG. 8

STABILIZATION MEMBER FOR STABILIZING BONES

BACKGROUND OF THE INVENTION

The invention relates to stabilization members for fixing broken or partly cracked bone parts during the healing process or an even longer period in a position in which the bone parts shall be stabilized and knit together, respectively.

The members consist of a bar having a plurality of elongated holes. Portions having a reduced cross-section can be provided between the elongated holes in order to allow the adaptation of the bar to the desired bone profile. The bar is fastened to the bone by means of screws which are screwed into the bone. Here the problem is encountered that only in rare cases the screws can be screwed in in a direction perpendicular to the bar, because the bone is irregularly formed and rarely comprises a sufficient cross-section in a direction perpendicular to the bar.

However, if the screw is screwed in in the direction of the largest cross-section of the bone, only one side of the screw head is supported in the elongated hole of the bar and the connection between the screw head and the bar is not sufficiently firm.

OBJECTS OF THE INVENTION

It is an object of the invention to provide an improved stabilization member in which the above-mentioned drawbacks are avoided. It is a further object of the invention to provide a stabilization member for stabilizing bones which provides a sufficient fixation for bones which are very irregularly formed.

SUMMARY OF THE INVENTION

According to the invention a stabilization member for stabilizing bones comprises a bar having a number of elongated holes therein, a number of screws extending through said elongated holes for fastening said bar to a bone part for the stabilization thereof, the screws having a screw head formed with a convex spherical segment-shaped bottom portion, and an intermediate piece having one side plainly resting on said bar and the other side being provided with a concave spherical segment-shaped recess receiving said bottom portion of said screws.

BRIEF DESCRIPTION OF THE DRAWINGS

Further advantages, features and objects of the invention will stand out from the following description of exemplary embodiments with reference to the drawings. In the drawings:

FIG. 1A shows a top view and FIG. 1B shows a side view of the inventive bar with inserted screws in connection with the intermediate piece according to the invention;

FIG. 2A represents a screw, FIG. 2B a plane view and FIG. 2C a side view of and one version of the inventive intermediate piece;

FIGS. 3 to 5 show the stabilization member in connection with a cervical vertebra stabilized thereby; and FIGS. 6 to 8 show a further embodiment of the intermediate piece, wherein FIG. 6 shows a section through the dismounted stabilization member, whereas FIG. 7 shows a section through the assembled member and FIG. 8 is a top view of the member of FIG. 7.

DESCRIPTION OF PREFERRED EMBODIMENTS

The bar 1 shown in FIG. 1 comprises a row of elongated holes 2 to $2^n$. In the region between the elongated holes the bar 1 can optionally comprise a series of portions 3 to $3^{n-1}$ having a reduced cross-section which allows the bar to be adapted to the shape of the bone (see for example FIG. 3).

A respective intermediate piece 7 is provided for each screw inserted through the elongated holes. The intermediate piece is placed onto the side of the bar 1 opposite to the bone at the desired position and serves for receiving the screw 4. The intermediate piece 7 comprises a bore 11 with a diameter which is larger than that of the shaft of the screw to be passed therethrough, so that the pivoting angle of the screw shaft is maximized. On the other hand the size of the bore is small enough to retain the screw head therein. The surface of the intermediate piece opposite to the bar 1 is formed with a spherical segment-shaped recess 8 which is concentric to the bore 11.

The screw 4 separately shown in FIG. 2 has a head 5 with a spherical segment-shaped portion 6 at the bottom side thereof which rests on or abuts the spherical segment-shaped recess 8 of the intermediate piece 7. The radii for the recess 8 and the portion 6 correspond to each other. This allows to screw in the screw 4 into the bone tissue at a spacial angle of up to about ±20°, as shown in the lower part of FIG. 1. Nevertheless, the entire screw head 5 fully contacts the intermediate piece 7 and by way thereof the bar 1, whereby a considerably improved stabilization is obtained.

The position and orientation of the screw 4 with respect to the bar 1 may be secured by providing, according to a further embodiment of the invention, the bottom side of the intermediate piece 7 and the top side of the bar 1 with a structuring or pattern. This structuring may, as shown in FIG. 1, be formed as a ribbing or a corrugation 9 perpendicular to the longitudinal direction of the bar 1.

This feature positively prevents a movement of the intermediate piece 7 and thus of the screw 4 after tightening the screw.

It is indicated in the middle part of FIG. 1 that the screw may be displaced within one and the same elongated hole 2, if desired.

FIGS. 3 to 5 show an embodiment of the invention when fastened to a cervical vertebra 10.

In FIG. 3 the bar 1 is buckled or bent at the weakened portions 3, 3', etc. having the reduced cross-section in order to adapt the bar to the shape or profile of the vertebra 10.

FIG. 4 shows an embodiment with a straight bar.

FIG. 5 shows a section through a cervical vertebra 10 which is stabilized with a respective stabilization member according to the invention at the right and left sides thereof.

A further version of the intermediate piece 7 is represented in the FIGS. 6 to 8.

According to this version the contour of the intermediate piece 7 laterally projects beyond the longitudinal sides of the bar 1 and comprises a shoulder 12 embracing the bar 1 on both sides thereof. This design improves the fixation of the intermediate piece 7 on the bar 1 and at the same time prevents a lateral displacement of the intermediate piece during the mounting thereof, whereby the operation is facilitated.

Although the invention has been described with reference to specific example embodiments, it is to be unterstood that it is intended to cover all modifications and equivalents within the scope of the appended claims.

What is claimed is:

1. Stabilization member for stabilizing bones, comprising a bar having a number of elongated holes therein, screws extending through said elongated holes for fastening said bar to a bone part for stabilization thereof, the screws having a screw head formed with a convex spherical segment-shaped bottom portion, and an intermediate piece having one side plainly resting on said bar and the other side being provided with a concave spherical segment-shaped recess receiving said bottom-portion of said screws.

2. The stabilization member of claim 1, comprising a structuring or pattern provided on the facing sides of said bar and said intermediate piece.

3. The stabilization member of claim 2, wherein said structuring comprises a ribbing or corrugation extending perpendicular to the longitudinal direction of said bar.

4. The stabilization member of claim 1, wherein said bar comprises spaced weakened portions having a reduced cross-section.

5. The stabilization member of claim 1, wherein said intermediate piece comprises two adjacent spherical recesses.

6. The stabilization member of claim 1, wherein said intermediate piece has a rectangular contour or outer shape.

7. The stabilization member of claim 1, wherein said intermediate piece has a round contour or outer shape.

8. The stabilization member of claim 1, wherein said elongated holes of said bar are bevelled at the side facing said bone.

9. The stabilization member of claim 1, wherein the contour of the intermediate piece projects beyond the longitudinal sides of said bar and comprises a shoulder embracing said bar on both sides thereof.

10. The stabilization member of claim 9, wherein said intermediate piece is bevelled at the side thereof facing said bar and rounded-off at the opposite side.

* * * * *